United States Patent [19]

Moreaud et al.

[11] 4,348,112
[45] Sep. 7, 1982

[54] METHOD OF AND APPARATUS FOR MEASURING THE VOLUME OF MATERIAL IN SUSPENSION IN A LIQUID

[75] Inventors: Henri Moreaud, Le Chesnay; Jean-Paul Meric, Paris, both of France

[73] Assignees: Omnium d'Assainissement, Courbevoie; Societe des Applications Biologiques du Laser a l'Environnement (SABLE) S.a.r.l., Paris, both of France

[21] Appl. No.: 116,766
[22] Filed: Jan. 30, 1980

[30] Foreign Application Priority Data

Jul. 13, 1979 [FR] France .............................. 79 18188

[51] Int. Cl.³ ............................................ G01N 21/00
[52] U.S. Cl. .................................... 356/338; 356/343
[58] Field of Search ................. 356/36, 336, 338, 341, 356/343; 210/93, 94, 95

[56] References Cited

U.S. PATENT DOCUMENTS

| 3,572,930 | 3/1971 | Morcom | 356/36 |
| 4,053,229 | 10/1977 | McCluney | 356/338 |
| 4,078,863 | 9/1978 | Eriksson et al. | 356/336 X |
| 4,110,043 | 8/1978 | Eisert | 356/336 |

FOREIGN PATENT DOCUMENTS 2701523 7/1978 Fed. Rep. of Germany ...... 356/343

7706318 11/1978 Sweden ................................ 356/341

Primary Examiner—John K. Corbin
Assistant Examiner—Matthew W. Koren
Attorney, Agent, or Firm—Browdy & Neimark

[57] ABSTRACT

A method of measuring volume of materials in suspensions in a liquid includes providing a sample of liquid containing particulate materials in suspension, passing a laser light beam through the liquid, the laser being diffracted upon exit from the sample, and measuring the diffracted light with at least two photoelectric cells positioned at differing distances from the central ray of the laser. Electrical signals F and F' from the photoelectric cells are produced and the volume (V) of materials in suspension is determined according to the relation $Vd = aF + a'F'$, where d is the average minimum diameter of the particles and a and a' are respective balancing factors. An apparatus for carrying out the method, particularly as it relates to determining the quality of water, includes raw water and flocculating agent sources upstream from a purification station and at least one coagulation-settling system, which includes a pipe coupled to the supply sources and a settling tank in which flocs settle. At least one laser diffractometer is coupled to said coagulation-settling system to receive continuously settled water therefrom, the laser diffractometer photoelectric cells for producing at least one signal representative of suspended materials remaining in the water.

6 Claims, 5 Drawing Figures

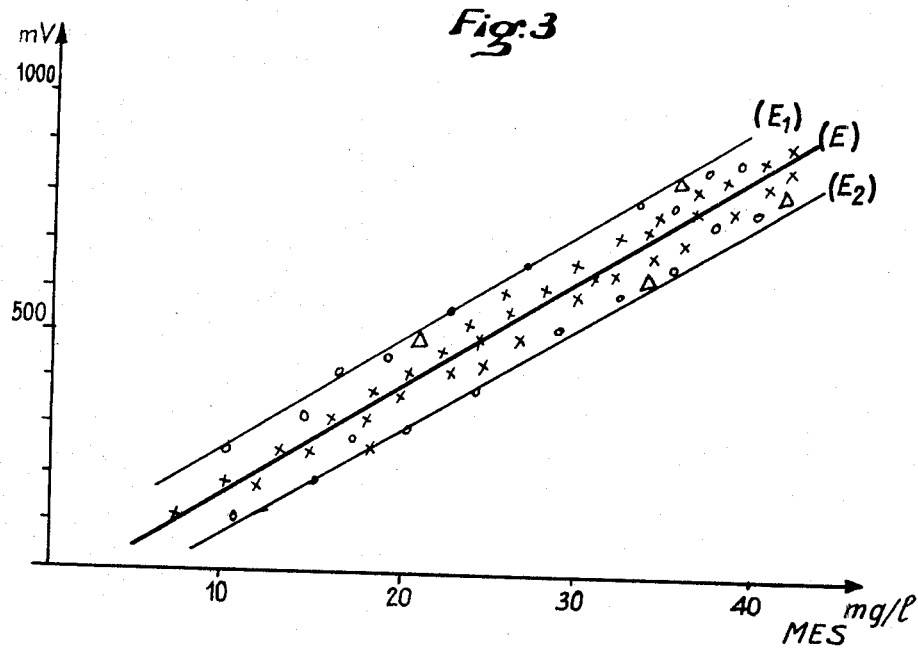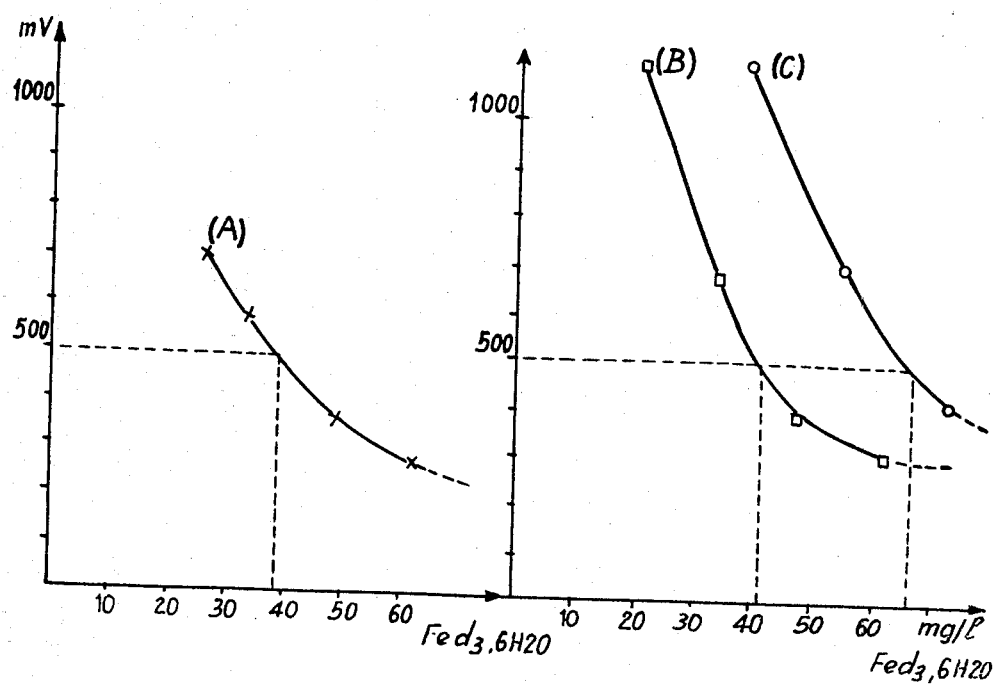

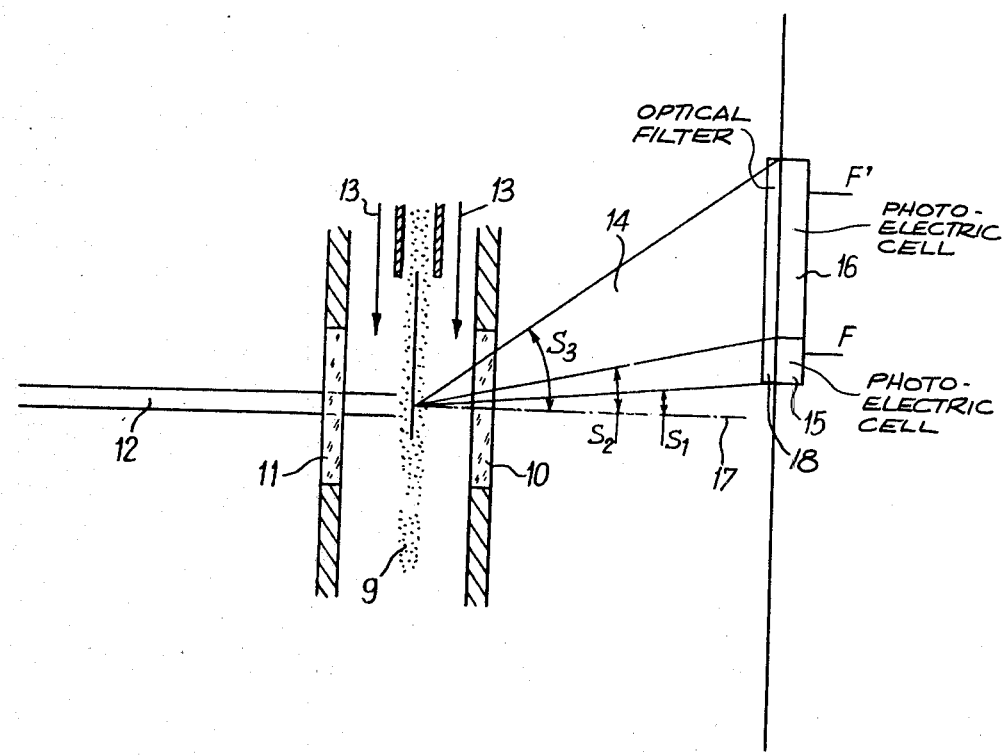

METHOD OF AND APPARATUS FOR MEASURING THE VOLUME OF MATERIAL IN SUSPENSION IN A LIQUID

BACKGROUND OF THE INVENTION

This invention relates to the field of determination of the volume of particles in suspension in a liquid, and particularly, checking of the functioning of liquid clarification installations. The present invention relates more particularly to a method of and apparatus for measuring the volume of particles of less than a predetermined size and application of this method, among other uses, to automatic measuring of the quality of a purified water, making it possible to determine the optimal amounts of a flocculating agent or agents use for coagulation-flocculation treatment of a waste water.

In numerous industries, for example, metallurgical, chemical, pharmaceutical, agriculture and food industries, or again in pollution control, a great number of techniques are used relating to dissolving, precipitation or flocculation of suspended solid particles. These techniques often require a measurement of the volume of materials suspended in a liquid.

It is known, for example, that in methods of clarifying liquids containing particles in suspension, which are too fine to be filtered or settled, it is generally necessary to provide a flocculating stage or system in which, by use of a suitable flocculating agent, as for example aluminum sulfate or ferric chloride in the case of water. Still, it is practically impossible to provide the exact dose of agent to be added and, if the physical and chemical characteristics of the liquid to be treated (for example, waste water) change over time, particularly in the case of industrial discharges or a dilution resulting from a storm, the dose initially selected for the flocculating agent is no longer suitable and the entire treatment is consequently compromised.

To mitigate the above-mentioned drawback, various techniques and apparatuses have been used or conceived. For example, methods have been proposed making possible the automatic delivery of the optimal dosage of the flocclating agent to be added to the raw water to be treated, thus replacing the laboratory testing, using a test known as th jar test.

In one known device, the turbidity of water is measured by producing signals which regulate the dosage of flocculating agent, based on a relation of correspondence between an increase of turbidity in the phase of floc formation and residual turbidity after settling. Several investigators have shown experimentally that there is a non-constant lag between the dose of reagent that gives maximum turbidity to the flocculated liquid and that which, after flocculation-settling, gives the most clarified liquid; this lag in practice causes an overdose of agent, a distinct shortcoming.

According to another technique, it has been proposed to check flocculation and automatically adjust the necessary amount of flocculating agent by optically measuring the volume of flocs by diffraction of a light beam produced by a laser. Use of a laser signal brings progress in comparison with the turbidimeter such as the one cited because the signal takes into account the different size of the particles and is insensitive to the color of the water. However, study of flocs does not constitute the most advantageous parameter for checking of flocculation and, moreover, this known technique does not make it possible to measure the volume of the materials in suspension in the liquid whose granulometry is less than a predetermined value.

SUMMARY OF THE INVENTION

The present invention aims at overcoming the above-mentioned shortcomings and difficulties and aims, by a measurement of the volume of materials in suspension (MIS) to determine precisely and rapidly the amount of small-sized particles in a liquid medium. It makes possible particularly, among other applications, a constant checking of the flocculation in a raw water purification station by measurement of the quality of the water obtained after flocculation and in which the surnatant particles generally have a size less than 10 microns.

The foregoing aims, as well as others which are to become clear from the text below, are achieved according to the present method, in its broad aspect, by providing a method of measuring the volume of materials in suspension of average diameter (d) less than a predetermined a value and is in essence characterized in that the diffracted light flux in at least two windows is measured using photoelectric cells, the maximum value of angle of diffraction s for the window closest to the central ray having to satisfy, for a helium-neon gas laser, the relation $s = (0.8/d)$, s being expressed in radians and d in microns. Electrical signals F and F' produced by and supplied from the photoelectric cells are then balanced and added to give a final signal proportional to the volume V of the materials in suspension according to the relation: $Vd = aF + a'F'$, a and a' being respectfully the balancing factors of the signals F and F'.

The balancing factors can be determined by calculation. However, preferably, these factors are determined empirically by using suspensions with as diverse granulometries as possible. For each sample, the signals supplied by the photoelectric cells and the volume of materials in suspension are measured. It is then possible to calculate the balancing factors by a linear regression. Analysis of the variance of the balancing factors and volume makes it possible to check to determine whether the windows are well chosen.

In practice of the present invention, the liquid to be studied is advantageously brought continously between two transparent strips and the diffraction attributable to the strips is measured periodically and used to correct the value obtained.

Preferably, a flow of protective liquid is continously brought in contact with the strips. This flow makes it possible to keep the materials in suspension from being deposited on the strips and thus falsify the measurement.

Advantageously, a monochromatic filter, permeable only to the light of a laser, is placed in front of the photoelectric cells and the laser beam is modulated, the electrical signal retained being that of the modulation frequency of the laser.

According to a preferred embodiment, the light beam of the laser is focused before going through the sample to be studied. Thus, it is possible to increase the precision of the measurement.

The method as disclosed above the lends itself to numerous applications each time it is desired to have, as the criterion of a given fluid medium, the total volume of particles suspended in a liquid. However, it is very specially suited to determination of the quality of water by measurement of its susceptability to flocculation with a view to fixing the precisely necessary amounts of a flocculating agent to be used to obtain coagulation from raw water.

According to the application mentioned above, there is taken, upstream from a water purification station, a continous sample of the raw water to be treated, feeding it, simultaneously with dosed amounts of a flocculating agent or agents into a coagulation-settling stage where the settling of flocs is accomplished in a few minutes and the volume of residual particles in suspension in the water separated from the flocs is measured by optical diffraction, by the particles, of the light beam from the abovementioned laser, the diffracted light being converted into an electrical signal in direct relation with the volume of particles which is compared with calibrating curves.

As a result of a series of systematic tests, it has been determined that it is actually possible to establish as a fact that simple mechanical agitation would make it possible to eliminate, after settling, almost all particles greater than 20 microns, and that the addition of chemical agents would improve the results and residual pollution of the surnatant liquid, expressed by be various measurements, for example, materials in suspension (MIS), total oxygen demand (TOD) turbidity and the like. The materials in suspension goes through a minimum as the flocculating agent is increased.

BRIEF DESCRIPTION OF THE DRAWINGS

FIG. 3 is a graph representing the relationship between diffractometer output and remaining materials in suspension after flocculation.

FIG. 4 is a graphical representation showing a family of curves which illustrate the differing characteristics which occurred over a period of a few hours in the relationship between the diffractometer output and remaining materials in suspension.

FIG. 5 is a diagramatic illustration of a laser diffractometer which may be used in the raw water circuit installation of FIG. 2.

DETAILED DESCRIPTION OF THE PREFERRED EMBODIMENTS

Figure 1:
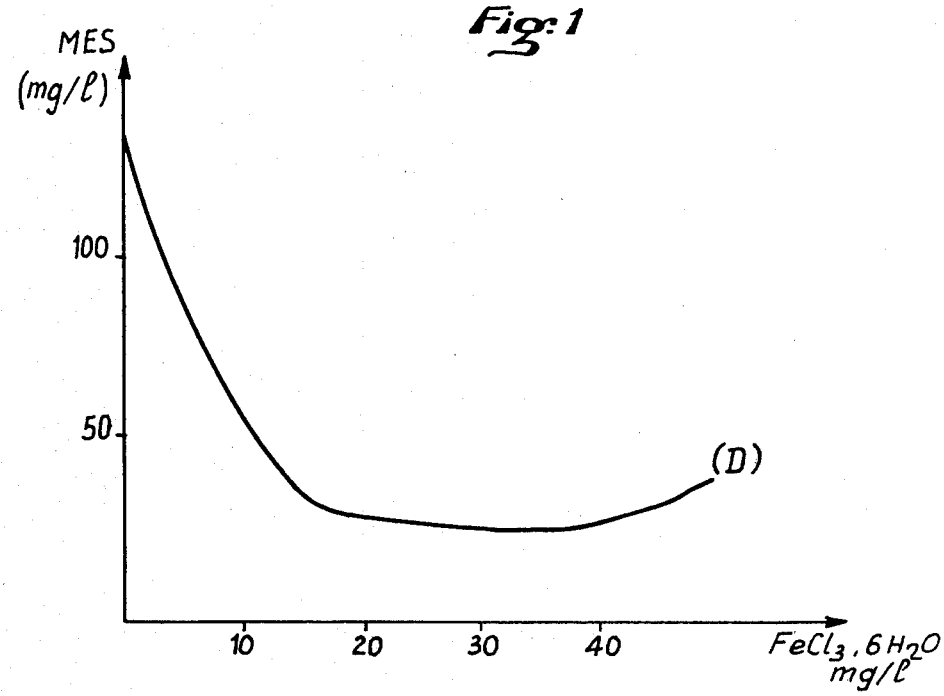
FIG. 1 is a graph representing the relationship between the materials in suspension and the amount of agent added.

The materials in suspension parameter, as pointed out above, goes through a minimum as the flocculating agent dose is increased. This optimum is most sensitive for the materials in suspension, as shown by curve (D) of FIG. 1. In the vicinity of this optimum point, the residual pollution is made up of particles of a size less than 10 microns and by dissolved molecules.

These tests made it possible to conclude that measurement of the materials in suspension, which furthermore is an official criterion of the quality of waste water after treatment, constituted the most significant parameter making it possible to optimize a method for checking the flocculation of a water.

Thanks to the present invention, it is possible to reach a precise and rapid determination, less than 15 minutes, of these materials in suspension (MIS).

The invention is better understood from the detailed description of non-limiting embodiments according to the examples set out below.

EXAMPLE 1

Measurement of a volume of a suspension with an apparatus according to the method of the present invention.

As can be seen in the schematic diagram of FIG. 5, a flat jet of liquid 9 of a sample, whose volume of materials in suspension it is desired to measure, passes between two transparent strips 10 and 11 and is illuminated by a laser beam 12. To protect the strips 10 and 11 from the materials in suspension contained in the jet liquid 9, there is provided a sweeping curtain of liquid 13 between the liquid 9 carrying the materials in suspension and the transparent strips 10 and 11.

Through the sample, the laser beam 12 is diffracted into a beam 14 whose intensity is measured in two diffraction windows provided with respective photoelectric cells and 15 and 16. The electrical signals F and F' coming respectively from the two cells 15 and 16 are then balanced and added to give a signal proportional to the volume of the materials in suspension with a granulometry less than a predetermined value d, to satisfy the relation: $Vd = aF + a'F'$, a and a' being balancing factors of the signals F and F'. A monochromatic filter 18, permeable only to the light wavelength produced by the laser is preferrably placed in front of the windows so that only light of the desired wave length strikes the photoelectric cells 15 and 16.

For example, to measure the volume of materials in suspension with a diameter less than 20 microns, regardless of the granulometry of the totality of the materials, the two diffraction windows are associated with the photoelectric cells selected whose values of diffraction angles s, in relation to the central incident ray 17, are such as: $S_1 = 0.04$, $S_2 = 0.10$ and $S_3 = 0.30$, these values being expressed in radians.

The precision with which the volume is obtained increases when the number of windows increases and decreases when the relative variations of the various granulametric populations are considerable. These variations, however, are slight and the angular limits of the diffraction windows are chose in relation to the granulometric populations. This relation can be written if for example a helium-neon laser is used, (for which $\lambda = 0.6328$ microns), $s = (0.8/d,)$, where d is the diameter of the particle in microns and s the angular limit in radians.

In FIG. 5, the sample is represented in the form of a flow between the two transparent strips 11 and 12. Under these conditions it is necessary to take into account the diffraction of the interfaces and periodically measure this diffraction in the absence of the sample to up-date and correct, the resulting value. However, the sample can also be in the form of a jet.

The apparatus can be made insensitive to interference by a modulation of the laser beam 12 obtained by an apertured disk turning at a constant speed. Further, an optical filter 18 can be placed in front of the photoelectric cells 15 and 16 to let light pass having only the wavelength of the laser. This arrangement makes it possible to use the apparatus in the open air.

EXAMPLE 2

Application of the method of the present invention to check continously the flocculation of raw water at a purification station.

Figure 2:
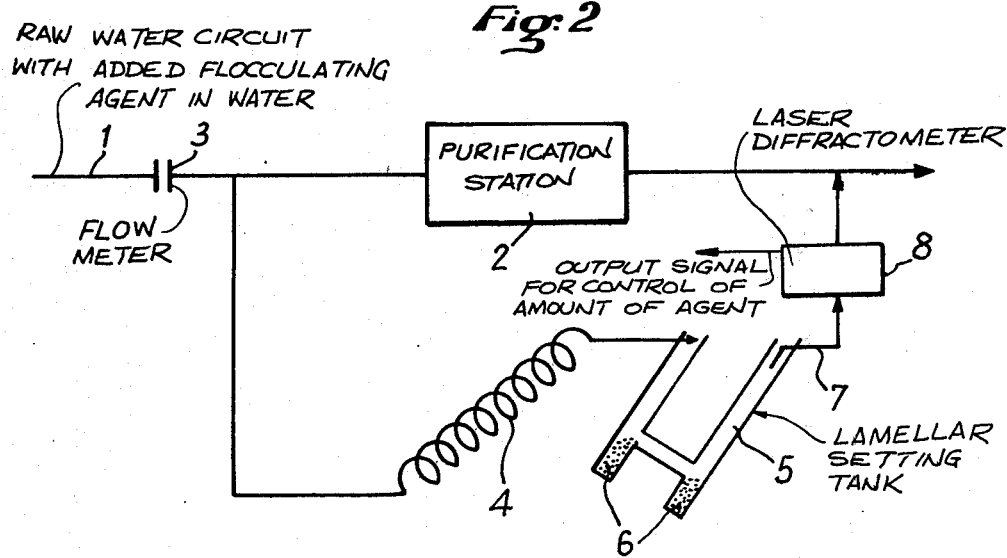
FIG. 2 is a schematic diagram of raw water circuit operatively associated with a laser diffractometer in accordance with the present invention.

To make the above-mentioned application, the installation outlined in the schematic diagram of FIG. 2 is advantageously used. A raw water circuit 1 coming to a purification station 2 and down stream from a flow meter 3 is branched to at least one coagulation settling system made up of the combination of a coiled pipe 4 and a lamellar settling tank 5. In practice, several of these systems are arranged in parallel, for example, three or four, each of which functions with a determined dose of flocculating agent to be able to plot, with the various measuring points, the curves establishing the relation between the laser signal and flocculating agent dose. The flocs accumulate at 6 in the lamellar settling tank 5, the surnatant liquid is passed on, via conduit 7 to a laser diffractometer 8 and passes through the diffractometer where electrical signals are produced which make it possible to determine the volume of particles and the amount of agent exactly necessary for flocculation. The laser diffractometer 8 can advantageously be constructed as the system illustrated in FIG. 5.

For testing properly so-called, first calibrating of the laser diffractometer 8 was undertaken by working on several urban waters flocculated with ferric chloride ($FeCl_3.6\ H_2O$) and by determining by weight, the amounts of solid materials remaining in suspension (MIS) in the surnatant liquid after flocculation, for each signal expressed in millivolts (mV) of the diffractometer 8. As indicated in FIG. 3 there was thus obtained a whole series of points that make it possible to plot the calibrating curve (E) with a slope corresponding to a ratio of laser signal (mV)/concentration (in mg/l) about a midpoint approximately equal to 30 of materials in suspension. As can be seen in FIG. 3, the dispersion of the measuring points around curve (E) is represented by two extreme straight lines ($E_1$) and ($E_2$); the correlation factor in on the order of 0.93 which can be considered as very exact in this field of measurements.

With this comparison curve available, numerous series of continous flocculation tests were made at the input of a raw water purification station (in this case, at the Colombes station, near Paris). The working wavelength of the laser was 0.632 microns. Further, four installations of coagulometers were used in parallel, these each being of the type shown in FIG. 2, with the following characteristics:

volume of coiled pipe 4, 500 ml (diameter 8 mm);
volume of lamellar settling tank 5, 500 ml;
inclination of settling tank 5, in relation to the horizontal, about 55 degrees; and
staying time varying from 7 to 15 minutes (generally, close to 10 minutes).

For each type of water the tests consisted in introducing increasing doses of the flocculating agents to determine the relation between the doses of flocculants and the quality of the treated water at a given moment. Starting with this relation, it is easy to fix the doses which should be applied as a function of the desired objective, i.e., either a technical and economic optimum or a concentration of 30 mg/l of materials in suspension, which corresponds to the rejection standard for urban waters. By way of illustrative example there are reproduced in FIG. 4, a family of curves obtained on raw water coming to the Colombes (France) station the same day at a number of different periods during the day. Curve (A) was obtained at 11:00 am; curve (B) was obtained at 3:00 pm; and curve (C) was obtained at 7:00 pm. Thus, it can be that the great variation of the doses of flocculating agent to be added to a water in a relatively short period. For a signal of the laser diffractometer 8 of 500 mV these doses went from 37 mg/l of $FeCl_3.6\ H_2O$ at 11:00 am to 42 mg/l around 3:00 pm and to 66 mg/l at 7:00 pm.

By working in parallel on an industrial installation for treating urban waste waters, there was found an excellent agreement between the results obtained from said installation and those that made possible the plotting of the curves mentioned above.

Of course, hundreds of other continous systematic tests were made and made it possible to establish that, the average time of plotting a curve of type A, B or C by four points being about 12 to 15 minutes, it was possible to adjust in a very short time the dose of flocculating agent exactly necessary for a continous delivery of raw water to be treated. Thus, this method makes it possible to avoid any waste of flocculating agents and always stay within a zone outside of underdoses or overdoses of the agents. This applies both to sewage or industrial waste waters and drinking waters, such as surface or other water.

What is claimed is:

1. A method for determining the quality of water by measurement of its flocculation susceptability with a view to fixing the precisely necessary amounts of flocculating agent to be used to obtain coagulation of a raw water to be treated in a purification station, comprising:
    adding a known amount of at least one flocculating agent to the raw water to be treated upstream of the purification station;
    taking, upstream of the purification station, a continuous sample of the raw water to which the flocculating agent has been added;
    causing said sample to pass into at least one coagulation-settling system where settling of flocs is effected in a few minutes;
    feeding water continuously out of said system into a laser diffractometer;
    producing an output signal from said laser diffractometer which is related to the volume of particulate materials in suspension in the water; and
    controlling the amount of flocculating agent or agents added to the water in said adding step as a function of said output signal.

2. An apparatus for automatically determining the quality of water which may contain materials in suspension, the apparatus comprising:
    raw water and flocculating agent supply means upstream from a purification station;
    at least one coagulation-settling system which includes a pipe coupled to said supply means and a settling tank in which flocs settle;
    one laser diffractometer coupled to said coagulation-settling system to receive continuously settled water therefrom, said laser diffractometer including means for producing at least one signal representative of suspended materials remaining in the water.

3. The apparatus according to claim 2, including means responsive to the signal from the laser diffractometer for controlling the amount of flocculating agent or agents to be added to the water.

4. The apparatus according to claim 2 or claim 3, wherein said settling tank is a lamellar settling tank.

5. The apparatus according to claim 2 or claim 3, wherein said pipe is a coiled pipe.

6. The apparatus according to claim 2 or claim 3, wherein said at least one coagulating system comprises at least three of such systems connected in parallel.

* * * * *

UNITED STATES PATENT AND TRADEMARK OFFICE
CERTIFICATE OF CORRECTION

PATENT NO. : 4,348,112
DATED : September 7, 1982
INVENTOR(S) : Moreaud et al.

It is certified that error appears in the above–identified patent and that said Letters Patent are hereby corrected as shown below:

Title page, [75] Inventors: - should read --Henri Moreaud, Le Chesnay, France--

Signed and Sealed this

Sixteenth Day of November 1982

[SEAL]

Attest:

GERALD J. MOSSINGHOFF

Attesting Officer

Commissioner of Patents and Trademarks